US012226391B2

(12) United States Patent
Gordon et al.

(10) Patent No.: US 12,226,391 B2
(45) Date of Patent: Feb. 18, 2025

(54) METHOD OF TREATING TUMOURS (71) Applicant: QBIOTICS PTY LTD, Taringa (AU)

(72) Inventors: Victoria Anne Gordon, Yungaburra (AU); Paul Warren Reddell, Yungaburra (AU); Glen Mathew Boyle, Taringa (AU); Jason Kingsley Cullen, Thornside (AU); Peter Gordon Parsons, St Lucia (AU)

(73) Assignee: QBIOTICS PTY LTD, Queensland (AU)

( * ) Notice: Subject to any disclaimer, the term of this patent is extended or adjusted under 35 U.S.C. 154(b) by 800 days.

(21) Appl. No.: 17/602,909

(22) PCT Filed: Apr. 9, 2020

(86) PCT No.: PCT/AU2020/050360
§ 371 (c)(1),
(2) Date: Oct. 11, 2021

(87) PCT Pub. No.: WO2020/206504
PCT Pub. Date: Oct. 15, 2020

(65) Prior Publication Data
US 2022/0193023 A1    Jun. 23, 2022

(30) Foreign Application Priority Data
Apr. 12, 2019   (AU) ................ 2019901280

(51) Int. Cl.
*A61K 31/336* (2006.01)
*A61K 9/00* (2006.01)
*A61P 35/00* (2006.01)

(52) U.S. Cl.
CPC .......... *A61K 31/336* (2013.01); *A61K 9/0014* (2013.01); *A61K 9/0019* (2013.01); *A61P 35/00* (2018.01)

(58) Field of Classification Search
CPC ............... A61K 31/336; A61K 9/0014; A61K 9/0019; A61P 35/00
See application file for complete search history.

(56) References Cited

FOREIGN PATENT DOCUMENTS

| WO | WO-2007070985 A1 | 6/2007 |
| WO | WO-2018018097 A1 | 2/2018 |
| WO | WO 2018/170559 A1 | 9/2018 |

OTHER PUBLICATIONS

Abuodeh, Y., et al., "Systematic Review of Case Reports on the Abscopal Effect," Current Problems in Cancer 40(1):25-37, Elsevier, Inc., United States (2016).
Adams, J.L., et al., "Big Opportunities for Small Molecules in Immuno-oncology," Nature Reviews Drug Discovery 14(9):603-622, Nature Pub. Group, England (2015).
Aznar, M.A., et al., "Intratumoral Delivery of Immunotherapy-Act Locally, Think Globally," Journal of Immunology 198(1):31-39, American Association of Immunologists, United States (2017).
Barnett, E.M.C., et al., "Optimising Intratumoral Treatment of Head and Neck Squamous Cell Carcinoma Models With the Diterpene Ester Tigilanol Tiglate," Investigational New Drugs 37(1):1-8, Springer, United States (2018).
Boutros, C., et al., "Safety Profiles of Anti-CTLA-4 and Anti-PD-1 Antibodies Alone and in Combination," Nature Reviews Clinical Oncology 13(8):473-486, Nature Publishing Group, England (2016).
Boyle, G.M., et al., "Intra-Lesional Injection of the Novel PKC Activator EBC-46 Rapidly Ablates Tumors in Mouse Models," Plos One 1;9(10):e108887, Public Library of Science, United States (2014), 12 pages.
Chalmers, Z.R., et al., "Analysis of 100,000 Human Cancer Genomes Reveals the Landscape of Tumor Mutational Burden," Genome Medicine 9(1):34, BioMed Central, England (2017), 14 pages.
Demaria, S., et al., "Ionizing Radiation Inhibition of Distant Untreated Tumors (Abscopal Effect) is Immune Mediated," International Journal of Radiation Oncology Biol. Phys. 58(3):862-870, Elsevier, United States (2004).
Eisenhauer, E.A., et al., "New Response Evaluation Criteria in Solid Tumours: Revised Recist Guideline (Version 1.1)," European Journal of Cancer 45(2):228-247, Elsevier Ltd., England (2009).
Gardner, H.L., et al., "Dogs as a Model for Cancer," Annual Review of Animal Biosciences, 4:199-222, Annual Reviews, United States (2016).
Gibney, G.T., et al., "Predictive Biomarkers for Checkpoint Inhibitor-Based Immunotherapy," Lancet Oncology 17(12):e542-e551, Lancet Pub, England (2016).
Goodman, A.M., et al., "Tumor Mutational Burden as an Independent Predictor of Response to Immunotherapy in Diverse Cancers," Molecular Cancer Therapeutics 16(11):2598-2608, American Association for Cancer Research, United States (2017).
Hammerich, L., et al., "In Situ Vaccination: Cancer Immunotherapy Both Personalized and Off-the-Shelf," Molecular Oncology 9(10):1966-1981, John Wiley & Sons, United States (2015).
Hammerich, L., et al., "In Situ Vaccination for the Treatment of Cancer," Immunotherapy 8(3):315-330, Future Medicine, England (2016).
Marabelle, A., et al., "Intratumoral Immunotherapy: Using the Tumor as the Remedy," Annals of Oncology : Official Journal of the European Society for Medical Oncology 28(suppl. 12):xii33-xii43, Oxford Press, England (2017).
Marabelle, A., et al., "Starting the Fight in the Tumor: Expert Recommendations for the Development of Human Intratumoral Immunotherapy (HIT-IT)," Annals of Oncology 29(11):2163-2174, Oxford Press, England (2018).
Marin-Acevedo, J.A., et al., "Next Generation of Immune Checkpoint Therapy in Cancer: New Developments and Challenges," Journal of Hematology & Oncology 15;11(1):39, Biomed Central, England (2018), 20 pages.
Marin-Acevedo, J.A., et al., "Next Generation of Immune Checkpoint Inhibitors and Beyond," Journal of Hematology & Oncology 19;14(1):45, Biomed Central, England (Mar. 2021), 29 pages.

(Continued)

*Primary Examiner* — Sikarl A Witherspoon
(74) *Attorney, Agent, or Firm* — Sterne, Kessler, Goldstein & Fox P.L.L.C.

(57) ABSTRACT

The present invention relates to methods of treating tumours comprising the localised administration, for example, intratumourally or topically, of an epoxytiglienone compound (as a monotherapy) to cancerous tumours to generate a systemic anticancer abscopal (anenestic) and/or bystander effect.

17 Claims, 2 Drawing Sheets

(56) References Cited

OTHER PUBLICATIONS

Mastrangelo, M.J., et al., "Intralesional BCG in the Treatment of Metastatic Malignant Melanoma," Cancer 37(2):684-692, Wiley, United States (1976).

Mastrangelo, M.J., "Regression of Pulmonary Metastatic Disease Associated With Intralesional BCG Therapy of Intracutaneous Melanoma Metastases," Cancer 36(4):1305-1308, Wiley, United States (1975).

Melendez, B., et al., "Methods of Measurement for Tumor Mutational Burden in Tumor Tissue," Translational Lung Cancer Research 7(6):661-667, Pioneer Bioscience Publishing Company, China (2018).

Miller, J., et al., "Dose Characterization of the Investigational Anticancer Drug Tigilanol Tiglate (EBC-46) in the Local Treatment of Canine Mast Cell Tumors," Frontiers in Veterinary Science 9(6):106, Frontiers Media, Switzerland (Apr. 2019), 10 pages.

Panizza, B.J., et al., "Phase I Dose-Escalation Study to Determine the Safety, Tolerability, Preliminary Efficacy and Pharmacokinetics of an Intratumoral Injection of Tigilanol Tiglate (EBC-46)," EBioMedicine 50:433-441, Elsevier, Netherlands (Dec. 2019).

Prise, K.M. and O'sullivan, J.M., "Radiation-induced Bystander Signalling in Cancer Therapy," Nature Reviews 9(5):351-360, Nature Publishing Group, England (2009).

Schumacher, T.N. and Schreiber, R.D., "Neoantigens in Cancer Immunotherapy," Science 348(6230):69-74, American Association for the Advancement of Science, United States (2015).

Yarchoan, M., et al., "Targeting Neoantigens to Augment Antitumour Immunity," Nature Reviews 17(4):209-222, Nature Pub, England (2017).

Yarchoan, M., et al., "Tumor Mutational Burden and Response Rate to PD-1 Inhibition," The New England Journal of Medicine 21;377(25):2500-2501, Massachusetts Medical Society, United States (2017).

Barnett, E.M.C., "Optimizing intratumoral treatment of head and neck squamous cell carcinoma mouse models with EBC-46," a Thesis submitted for the degree of Master of Philosophy at The University of Queensland, The University of Queensland School of Medicine, Australia (2015).

International Preliminary Report on Patentability for International Application No. PCT/AU2020/050360, mailed on Feb. 8, 2021, Australian Patent Office, Australia, 4 pages.

International Search Report for International Application No. PCT/AU2020/050360, mailed on May 4, 2020, Australian Patent Office, Australia, 5 pages.

Written Opinion of the International Searching Authority for International Application No. PCT/AU2020/050360, mailed on May 4, 2020, Australian Patent Office, Australia, 5 pages.

METHOD OF TREATING TUMOURS

FIELD OF THE INVENTION

The present invention relates to the localised administration, for example, intratumourally or topically, of an epoxytiglienone compound (as a monotherapy) to cancerous tumours to generate a systemic anticancer abscopal and/or bystander effect.

BACKGROUND OF THE INVENTION

Abscopal effects are a phenomenon observed in some metastatic cancers and involve the spontaneous regression of untreated non-adjacent and distant tumours following a localised treatment delivered to one or more target tumours.

The term abscopal, first introduced in the 1950s, is derived from the Latin (ab:"away from" and scopus: "target") and was used in reference to the regression of tumours distant from a primary site treated by radiotherapy. In the radiotherapy literature, abscopal effects are distinguished from a second type of 'off-target' response, the bystander effect, which occurs only in cells neighbouring the treated tumour (Prise and O'Sullivan 2009). Bystander and abscopal effects differ in their underlying causal mechanisms. Bystander effects are due primarily to cellular stress signalling involving reactive oxygen species and the release of cytokines (e.g. transforming growth factor-$\beta 1$, tumour necrosis factor-$\alpha$) and death ligands that are transmitted directly to cells adjacent to the irradiated treatment field (Prise and O'Sullivan 2009). In contrast, abscopal effects are mediated by the immune system and involve induction of an inflammatory response, necrosis of the irradiated tumour cells, stimulation of dendritic cells and activation of cytotoxic T cells (Demaria et al. 2004).

Abscopal effects induced by radiation monotherapy have been reported for several cancers including melanoma, squamous cell carcinoma, renal cell carcinoma, breast adenocarcinoma, hepatocellular carcinoma, Merkel cell carcinoma, medullary carcinoma and lymphocytic lymphoma (Abuodeh et al. 2016). Prior to 2010, there were also a small number of reports of abscopal effects associated with other locally administered monotherapies including photodynamic therapy and some intratumourally-delivered agents such as Bacillus Calmette-Guerin (BCG) e.g. Mastrangelo et al. 1975. However, when radiation or these other locally administered therapies were used alone, abscopal events were exceedingly rare and largely unpredictable. For example, a review of reported abscopal effects in radiation monotherapy found only 46 case reports between 1969 and 2014, despite millions of patients being treated worldwide (Abuodeh et al. 2016). Not surprisingly, the abscopal effect remained a relatively obscure and largely ignored phenomenon until the advent of cancer immunotherapy.

Following scientific breakthroughs in the understanding of the role of the immune system in cancer, targeting and modulating immune responses in cancer has become a key focus in the development of new anticancer therapeutics. The first wave of these new immunomodulating therapies, both systemically and locally delivered treatments, have reached the clinic and abscopal effects are being increasingly reported. Indeed, systemic abscopal effects are fundamental for efficacy of some treatments such as intratumourally-delivered oncolytic viruses e.g. FDA-approved talimogene laherparepvec (T-VEC) for treatment of advanced melanomas. Based on the success, and some of the limitations, of these first-generation immunotherapies there is strong interest in identifying further immuno-oncology agents. One group of strategies involves the use of intratumoural treatments (either alone or in combination with other treatment modalities) to induce a strong local priming of cancer immunity that converts immunosuppressed ('cold' tumours) into immunostimulatory or 'hot' tumours that then generate systemic abscopal effects through circulation of properly activated anti-tumour immune cells (Aznar et al. 2016; Marabelle et al. 2017). In essence these approaches aim to use the locally-treated tumour as its own 'in situ vaccine' to generate an abscopal effect in untreated tumours (Hammerich et al. 2015). A range of possible mechanisms are being explored to facilitate this immune priming, including directly activating effector functions of innate and adaptive immune cells, inhibiting the highly immunosuppressive tumour microenvironment, enhancing antigen release and presentation by living tumour cells, or stimulating regulated forms of tumour cell death that elicit adaptive immune responses against dead tumour cell-associated antigens. Examples of current agents under investigation for use as such intratumoural immunostimulants include oncolytic viruses and peptides, attenuated bacterial vaccines, cytokines (e.g. IL-2, IL-12, granulocyte-macrophage colony-stimulating factor), immune system cells (e.g. dendritic cells, chimeric antigen receptor T-cells), pattern recognition receptor agonists (e.g. Toll-like receptor (TLR) agonists such as imiquimod), a small group of conventional cytotoxic chemotherapeutics (e.g. doxorubicin, oxaliplatin, cyclophosphamide) and immune checkpoint targeted antibodies (e.g anti-CTLA-4). However, there are significant potential technical and practical hurdles for eventual translation of many of these agents into widespread clinical use, especially for biologics with their relatively high cost and possible adverse immunological toxicities (e.g. Boutros et al. 2016; Marin-Acevedo et al 2018). This has led to the suggestion that small molecules have been largely neglected in the search for new immuno-oncology agents and that they may offer several unique technical and commercial advantages including providing access to intracellular disease targets not tractable by biological immunotherapies together with their ease of use, generally lower cost and simpler supply chains (Adams et al. 2015).

Epoxytiglienones are potent anti-tumour compounds that are active against a range of cancer types in vivo (Boyle et al. 2014; Barnett et al. 2019; Miller et al. 2019). Epoxytiglienones are administered as a local monotherapy, either intratumourally or topically, with dosing of the target tumour based on tumour size (Miller et al. 2019). Epoxytiglienones destroy the tumours to which they are administered by inducing rapid haemorrhagic necrosis of the tumour mass including by oncosis of tumour cells and disruption of tumour vasculature (Boyle et al. 2014). Epoxytiglienones act at the local treatment site at which they are administered with no expectation of a systemic response when they are delivered as a monotherapy. For example, in the protocol for recently completed first-in-human Clinical Phase I trials using the prototype epoxytiglienone compound tigilanol tiglate (Panizza et al. 2019), where multiple tumours were available to be treated within the constraints of a dose cohort, the drug was required to be administered to each tumour individually to ensure potential efficacy. Recently (WO2018/170559, Example 7, FIG. 7B) in a stringent syngeneic, immunocompetent mouse model of melanoma it was demonstrated that epoxytiglienone compounds used in combination with immune checkpoint inhibitors (ICIs) more effectively ablated not only the locally-treated target tumour but also some adjacent untreated tumours. This systemic effect was not observed in this, or other mouse tumour models that have been tested, when either agent (the epoxytiglienone or the ICIs) were used alone.

The present invention is predicated on the unexpected discovery, in clinical studies in human and canine patients, that epoxytiglienone compounds when delivered as local monotherapy to one or more target tumours, in a number of immunogenic cancer types (i.e. cancer types known to have high mutational burden), can also stimulate a systemic abscopal effect and ablate non-adjacent and distant metastatic tumours to which drug had not been administered.

SUMMARY OF THE INVENTION

In one aspect of the present invention, there is provided a method of stimulating tumour regression in at least one non-target tumour in a subject with multiple tumours, said method comprising administering to at least one target tumour a 6,7-epoxytiglienone compound or a pharmaceutically acceptable salt thereof; wherein the at least one target tumour and the at least one non-target tumour are immunogenic tumours, and wherein administration is localised administration to the at least one target tumour.

In another aspect of the invention there is provided a use of a 6,7-epoxytiglienone compound or a pharmaceutically acceptable salt thereof in the manufacture of a medicament for stimulating tumour regression in at least one non-target tumour in a subject with multiple tumours; wherein the medicament is for localised administration to at least one target tumour and the at least one target tumour and at least one non-target tumour are immunogenic tumours.

In a further aspect of the invention, there is provided a 6,7-epoxytiglienone compound or a pharmaceutically acceptable salt thereof for use in stimulating tumour regression in at least one non-target tumour in a subject with multiple tumours; wherein the 6,7-epoxytiglienone compound is for localised administration to at least one target tumour and the at least one target tumour and at least one non-target tumour are immunogenic tumours.

BRIEF DESCRIPTION OF THE FIGURES

FIG. 1 is a graphical representation of the response of treated (squares) and untreated (circles) B16-F10 tumours in control individuals in which one tumour was treated with vehicle (a) and individuals in which one tumour was treated with 7.5 μg of Compound 1 (b).

FIG. 2 is a graphical representation of the response of treated (squares) and untreated (circles) Panc02 tumours in control individuals in which one tumour was treated with vehicle (a) and individuals in which one tumour was treated with 7.5 μg of Compound 1 (b).

DETAILED DESCRIPTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The term "alkyl" refers to optionally substituted linear and branched hydrocarbon groups having 1 to 20 carbon atoms. Where appropriate, the alkyl group may have a specified number of carbon atoms, for example, —$C_1$-$C_6$ alkyl which includes alkyl groups having 1, 2, 3, 4, 5 or 6 carbon atoms in linear or branched arrangements.

Non-limiting examples of alkyl groups include methyl, ethyl, propyl, isopropyl, butyl, s- and t-butyl, pentyl, 2-methylbutyl, 3-methylbutyl, hexyl, 2-methylpentyl, 3-methylpentyl, 4-methylpentyl, 2-ethylbutyl, 3-ethylbutyl, heptyl, octyl, nonyl, decyl, undecyl, dodecyl, tridecyl, tetradecyl and pentadecyl.

The term "alkenyl" refers to optionally substituted, unsaturated linear or branched hydrocarbons, having 2 to 20 carbon atoms and having at least one double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, pentenyl, hexenyl, hept-1,3-diene, hex-1,3-diene, non-1,3,5-triene and the like.

The term "alkynyl" refers to optionally substituted unsaturated linear or branched hydrocarbons, having 2 to 20 carbon atoms, having at least one triple bond. Where appropriate, the alkynyl group may have a specified number of carbon atoms, for example, $C_2$-$C_6$ alkynyl which includes alkynyl groups having 2, 3, 4, 5 or 6 carbon atoms in linear or branched arrangements. Non-limiting examples include ethynyl, propynyl, butynyl, pentynyl and hexynyl.

The terms "cycloalkyl" and "carbocyclic" refer to optionally substituted saturated or unsaturated mono-cyclic, bicyclic or tricyclic hydrocarbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

"Aryl" means a $C_6$-$C_{14}$ membered monocyclic, bicyclic or tricyclic carbocyclic ring system having up to 7 atoms in each ring, wherein at least one ring is aromatic. Examples of aryl groups include, but are not limited to, phenyl, naphthyl, tetrahydronaphthyl, indanyl and biphenyl. The aryl may comprise 1-3 benzene rings. If two or more aromatic rings are present, then the rings may be fused together, so that adjacent rings share a common bond.

Each alkyl, alkenyl, alkynyl, cycloalkyl or aryl whether an individual entity or as part of a larger entity may be optionally substituted with one or more optional substituents selected from the group consisting of $C_{1-6}$alkyl, $C_{2-6}$alkenyl, $C_{3-6}$cycloalkyl, oxo (=O), —OH, —SH, $C_{1-6}$alkylO—, $C_{2-6}$alkenylO—, $C_{3-6}$cycloalkylO—, $C_{1-6}$alkylS—, $C_{2-6}$alkenylS—, C$_{3-6}$cycloalkylS—, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, —CN, —NO$_2$, -halogen, —CF$_3$, —OCF$_3$, —SCF$_3$, —CHF$_2$, —OCHF$_2$, —SCHF$_2$, -phenyl, —C$_{1-6}$alkylphenyl, —Ophenyl, —C(O)phenyl, —C(O)C$_{1-6}$alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —CO$_2$H, —CO$_2$CH$_3$, —C(O)CH$_3$, trifluoromethyl, trifluoromethoxy, trifluoromethylthio, difluoromethyl, difluoromethoxy, difluoromethylthio, morpholino, amino, methylamino, dimethylamino, phenyl, phenoxy, phenylcarbonyl, benzyl and acetyl.

The epoxytiglienone compounds may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will also be recognised that the epoxytiglienone compounds may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be obtained by isolation from natural sources, by asymmetric synthesis, for example using chiral intermediates, or by chiral resolution. The compounds of the invention may exist as geometrical isomers. The invention also relates to compounds in substantially pure cis (Z) or trans (E) forms or mixtures thereof.

The compounds of the present invention may be obtained by isolation from a plant or plant part, or by derivatisation of the isolated compound, or by derivatisation of a related compound. Isolation procedures and derivatisation procedures may be found in WO 2007/070985 and WO2014/169356.

The term "6,7-epoxytiglienone compound" refers to a compound having the following carbon cyclic structure:

The compounds have a tricyclo[9.3.0.0]tetradecane system with a fused cyclopropane ring appended to the six membered ring. The epoxide is fused to the seven membered ring in the 6,7-position and the five membered ring has a 1,2-ene-3-one structure.

As used herein, the term "target tumour" refers to a tumour to which the 6,7-epoxytiglienone compound is directly administered in a localised manner.

The term "non-target tumour" as used herein, refers to a tumour to which the 6,7-epoxytiglienone compound has not been directly administered in a localised manner.

Although no direct localised administration occurs to the non-target tumour, the regression of the non-target tumour occurs subsequently to administration directly to the target tumour.

As used herein, the term "primary tumour" refers to the first tumour to arise in the subject.

The term "metastatic tumour" or "secondary tumour" as used herein, refers to a tumour that is derived from a primary tumour but has grown in a site different to the site of the primary tumour. A metastatic or secondary tumour may be located in the same organ or site as the primary tumour or may be located in a different organ or site from the primary tumour. A metastatic or secondary tumour contains the same lineage of tumour cells as the primary tumour.

A satellite tumour refers to a discrete tumour that is located at a site within 1 centimetre of the primary tumour. A satellite tumour could be a metastatic tumour, or in the case of UV-induced cutaneous squamous cell carcinomas and cutaneous haemangiosarcomas, a tumour that has differentiated de novo from a pre-cancerous field of solar keratoses.

The term "bystander effect" as used herein, refers to the death of tumour cells or regression of tumours located adjacent to a target tumour being treated. Tumour cells susceptible to the bystander effect, although not directly treated, neighbour or are in a close proximity to the target tumour such that they come into contact with cellular signalling released from the target tumour cells such as reactive oxygen species, cytokines and death ligands.

As used herein the term "abscopal effect" refers to the regression of tumours that are non-adjacent to, or located at a site distant from, the site to which a localised therapy is administered. Tumours susceptible to the abscopal effect are considered to be discrete tumours that are not in close proximity to (i.e. greater than 2 cm distant from) the target tumours being treated and the effects are mediated by an immune response.

Recently new terminology has been proposed for abscopal effects, target tumours and non-target tumours as they specifically relate to intratumourally-delivered immunotherapies (Marabelle et al., 2018). This terminology aims to distinguish abscopal effects that occur outside of the field of irradiation following radiotherapy, from effects that occur in non-treated tumours following delivery intratumourally of therapies into target tumours. Under these proposals it has been suggested that the term "abscopal effect" be replaced where intratumoural therapies are involved with "anenestic immune responses" and "anenestic tumour responses" (Marabelle et al., 2018). As used herein, the term "abscopal effect" refers to anenestic immune responses and anenestic tumour responses. The enestic tumour lesion, which has undergone intratumoural injection, is referred to herein as "target tumour" and the anenestic tumour lesion, which is an uninjected tumour lesion, is referred to herein as the "non-target tumour".

As used herein, the term "localised administration" refers to administration directly to the target tumour. For example, the localised administration may be topical administration or intratumoural administration where the therapeutic agent is injected directly into the tumour.

The term "tumour regression" as used herein refers to the partial or complete disappearance of the tumour. In some instances, complete tumour regression may occur and the tumour disappears. In other instances, partial tumour regression may occur and the tumour reduces in size but does not completely disappear.

Method of Stimulating Tumour Regression

The present invention relates to a method of stimulating tumour regression in at least one non-target tumour in a subject with multiple tumours, said method comprising administering to at least one target tumour a 6,7-epoxytiglienone compound or a pharmaceutically acceptable salt thereof; wherein the at least one target tumour and the at least one non-target tumour are immunogenic tumours, and wherein administration is localised administration to the at least one target tumour.

In some embodiments, the 6,7-epoxytiglienone compound or a pharmaceutically acceptable salt thereof is administered to one target tumour. In some embodiments, the 6,7-epoxytiglienone compound is administered to a primary tumour. In some embodiments, the 6,7-epoxytiglienone compound is administered to a secondary tumour. In other embodiments, the 6,7-epoxytiglienone compound or a pharmaceutically acceptable salt thereof is administered to more than one target tumour, for example, 2 to 20 tumours, including 2, 3, 4, 5, 6, 7, 8, 9, 10, 11, 12, 13, 14, 15, 16, 17, 18 19 or 20 tumours. The target tumours may be located in one organ or at one site in or on the subject, for example. a primary tumour and one or more satellite tumours or the target tumours may be located in multiple organs or at multiple sites in or on the subject. For example, the more than one target tumour may be located in different organs or at different sites such as a neck tumour and a tumour located on an arm. The more than one target tumour may be a primary tumour and one or more secondary tumours or the more than one target tumour may be more than one secondary tumour.

The 6,7-epoxytiglienone compound is locally administered to the at least one target tumour. In particular embodiments, the administration is intratumoural administration. In other embodiments, the administration is topical administration. In some embodiments, the tumour is a cutaneous tumour or subcutaneous tumour or a tumour accessible from the outside of the body, for example, a tumour that is palpable. In other embodiments, the tumour is an internal tumour. In some embodiments where the tumour is an internally located tumour, the localised delivery may be achieved during surgery when the tumour is exposed and able to be locally administered with the epoxytiglienone compound. In other embodiments, the tumour is internally located and the epoxytiglienone compound is delivered by injection guided by an imaging technique, for example, guided by endoscopic ultrasound or by stereotactic imaging. In particular embodiments, the tumour is accessible from the outside of the body.

In some embodiments, the at least one non-target tumour is a single tumour. In some embodiments there is one non-target tumour. In other embodiments, the at least one non-target tumour is more than one tumour, for example, 2 to 20 tumours, including 2, 3, 4, 5, 6, 7, 8, 9, 10, 11, 12, 13, 14, 15, 16, 17, 18 19 or 20 tumours. The non-target tumours may be located in one organ or at one site in or on the subject, for example. a primary tumour and one or more satellite tumours or the non-target tumours may be located in multiple organs or at multiple sites in or on the subject. For example, the more than one non-target tumour may be located in different organs or at different sites such as a neck tumour and a tumour located on an arm. The more than one non-target tumour may be a primary tumour and one or more secondary tumours or the more than one non-target tumour may be more than one secondary tumour. In some embodiments, the at least one non-target tumour is at least one bystander tumour. In particular embodiments, the non-target tumour is at least one tumour distant from the site of the target tumour and is susceptible to an abscopal effect. In some embodiments, the at least one non-target tumour is at least one bystander tumour and at least one tumour distant from the site of the target tumour that is susceptible to an abscopal effect.

The at least one target tumour and the at least one non-target tumour are immunogenic tumours. Immunogenic tumours are tumours susceptible to mediation by the immune system. For example, treatment of a target tumour may involve induction of an inflammatory response, necrosis of the tumour cells, stimulation of dendritic cells and activation of cytotoxic T cells and the non-target tumour is susceptible to the resulting immune responses occurring in the body. Immunogenic tumours are characterised by having a high tumour mutational burden (TMB). High TMB is a quantitative measure of the total number of somatic non-synonymous mutations per coding area of a tumour genome. TMB may be measured in a tumour by whole genome sequencing (WGS) or gene-targeted sequencing (Meléndez et al., 2018). It is postulated that tumour cells with high TMB have more neoantigens that can be recognised by cancer-fighting T cells in the tumour microenvironment. The recognition of the neoantigens by the T cells stimulates an anti-tumour immune response.

The intrinsic immunogenicity of cancer cells relies on their ability to induce a specific tumour-targeting immune response. Such immunogenicity is driven primarily by somatic mutations that cause cancer cells to express tumour-specific mutant proteins (called neo-antigens) that are not expressed in normal cells. The frequency of such mutations, and hence the potential neo-antigenicity of tumour cells, has been demonstrated to differ markedly between different cancer types (Schumacher & Streiber, 2015). TMB is a widely accepted surrogate measure of this potential neo-antigenicity (Gibney et al., 2016), with intermediate to high TMB shown to predict favourable outcome across a range of tumour types in patients treated with monoclonal antibodies that inhibit programmed death1 (PD-1) or its ligand (Goodman et al. 2017; Yarchoan et al. 2017). Using published data on TMB derived from 100,000 human genomes (Chalmers et al. 2017), the specific cancer types that will have the highest likelihood of generating a systemic abscopal effect in untreated tumours following administration of epoxytiglienone compounds to one or more 'target' tumours may be predicted. Of the 167 cancer types listed in Chalmers et al., 36 cancer types with intermediate to high TMB (as defined by Goodman et al. 2017) were identified on the basis of having (1) a median of more than 5 mutations per megabase or (2) more than 10% of cases have greater than 20 mutations per megabase. In some embodiments, the immunogenic tumour is a tumour having medium to high TMB as defined by either having a median of more than 5 mutations per megabase or having more than 10% of cases having greater than 20 mutations per megabase.

In some embodiments, the immunogenic tumour is selected from a melanoma, a basal cell carcinoma, a squamous cell carcinoma, a Merkel cell carcinoma, a lung carcinoma, a bladder carcinoma, a lymphoma, a breast adenocarcinoma, a hepatocellular carcinoma, a renal cell carcinoma, a medullary carcinoma, a colorectal cancer, a histiocytic sarcoma, a haemangiosarcoma or a mastocytoma (mast cell tumour). In some embodiments, the immunogenic tumour is selected from melanoma, including primary melanoma and head and neck melanoma, cutaneous basal cell carcinoma (BCC), cutaneous squamous cell carcinoma (SCC), head and neck squamous cell carcinoma, oesophagus squamous cell carcinoma, lung squamous cell carcinoma, anus squamous cell carcinoma, rectal squamous cell carcinoma, cervix squamous cell carcinoma, vulva squamous cell carcinoma, colorectal cancer, Merkel cell carcinoma, lung large cell carcinoma, lung large cell neuroendocrine carcinoma, lung small cell undifferentiated carcinoma, lung non-small cell lung carcinoma, lung sarcomatoid carcinoma, lung adenocarcinoma, lung adenosquamous carcinoma, bladder carcinoma, bladder urothelial transitional cell carcinoma (TCC), primary urothelial carcinoma, ureter urothelial carcinoma, lymph node lymphoma diffuse large B cell, lymph node lymphoma B-cell, lymph node lymphoma follicular lymphoma, primary sarcomatoid carcinoma, kidney urothelial carcinoma, stomach adenocarcinoma intestinal type, uterus endometrial adenocarcinoma, soft tissue angiosarcoma, skin adnexal carcinoma, oesophagus carcinoma and gastroesophageal junction adenocarcinoma. In particular embodiments, the immunogenic tumour is selected from cutaneous basal cell carcinoma (BCC), cutaneous squamous cell carcinoma (SCC), primary squamous cell carcinoma, melanoma, primary melanoma, head and neck melanoma, Merkel cell carcinoma, lung large cell carcinoma lymph node lymphoma diffuse large B cell and soft tissue angiosarcoma, especially cutaneous basal cell carcinoma (BCC), cutaneous squamous cell carcinoma (SCC), melanoma, lymph node lymphoma diffuse large B cell and soft tissue angiosarcoma.

The subject that may be treated with the combination therapy is a mammal, a bird, an aquatic animal such as a fish, or a reptile. In some embodiments, the subject is a human, a laboratory animal such as a primate, mouse, rat or rabbit, a companion animal such as a dog or cat, a working animal such as a horse, donkey and the like, a livestock animal such as a cow, bull, pig, sheep, goat, deer, llama, alpaca and the like, or a captive wild animal such as those in zoos or wildlife parks including lions, leopards, cheetah, elephant, zebra, antelope, giraffe, koala, kangaroo and reptiles such as crocodiles, lizards, snakes and the like, a bird, especially a captive bird, such as a budgerigar or canary, cockatoo, parakeet, macaw, parrot and the like, or a fish, especially a captive fish such as tropical fish (zebra fish, guppy, Siamese fighting fish, clown fish, cardinal tetra and the like), dolphins, whales, and the like. In particular embodiments, the subject is a human or a companion animal.

An "effective amount" means an amount necessary at least partly to attain the desired response, such as tumour regression. The amount varies depending upon the health and physical condition of the individual to be treated, the taxonomic group of individual to be treated, the formulation of the composition, the assessment of the medical situation, and other relevant factors. It is expected that the effective amount of 6,7-epoxytiglienone compound will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage.

The 6,7-epoxytiglienone compound is administered in a localised manner to a tumour. The dose administered is calculated based on tumour size. In general, the drug is administered in an amount of 5% to 50% volume of the drug 6,7-epoxytiglienone solution: the volume of the tumour. The solution of 6,7-epoxytiglienone compound is generally at a concentration between 0.2 to 5 mg/mL, for example, 0.5 to 2 mg/mL or 1 to 1.5 mg/mL. In some embodiments, the doses of 6,7-epoxytiglienone compound are in the range of 0.005 mg to 5.0 mg compound per cubic cm of tumour volume, especially 0.01 mg to 2 mg compound per cubic cm of tumour volume, more especially 0.1 mg to 0.75 mg compound per cubic cm of tumour volume.

Dosage regimes may be adjusted to provide the optimum therapeutic response.

The dose of 6,7-epoxytiglienone compound may be a single dose administered to each target tumour based on the tumour size. In some embodiments, the dose may be repeated at one or more subsequent times if complete response to the initial dose was not obtained in the target tumour. At a subsequent time, the 6,7-epoxytiglienone compound may be locally administered to the non-target tumour if complete response was not obtained with the initial dose administered to the target tumour.

6,7-Epoxytiglienone Compounds

In some embodiments, the 6,7-epoxytiglienone compound is a compound of formula (I):

(I)

or a geometric isomer or stereoisomer or a pharmaceutically acceptable salt thereof;

wherein
R$_1$ is hydrogen or C$_{1-6}$alkyl;
R$_2$ is —OR$_9$;
R$_3$ is —OH or —OR$_9$;
R$_4$ and R$_5$ are independently selected from hydrogen and C$_{1-6}$alkyl;
R$_6$ is hydrogen or —R$_{10}$;
R$_7$ is hydroxy or —OR$_{10}$;
R$_8$ is hydrogen or C$_{1-6}$alkyl;
R$_9$ is —C$_{1-20}$alkyl, —C$_{2-20}$alkenyl, —C$_{2-20}$alkynyl, —C(O)C$_{1-20}$alkyl, —C(O)C$_{2-20}$alkenyl, —C(O)C$_{2-20}$alkynyl, —C(O)cycloalkyl, —C(O)C$_{1-10}$alkylcycloalkyl; —C(O)C$_{2-10}$alkenylcycloalkyl, —C(O)C$_{2-10}$alkynylcycloalkyl, —C(O)aryl, —C(O)C$_{1-10}$alkylaryl, —C(O)C$_{2-10}$alkenylaryl, —C(O)C$_{2-10}$alkynylaryl, —C(O)C$_{1-10}$alkylC(O)R$_{11}$, —C(O)C$_{2-10}$ alkenylC(O)R$_{11}$, —C(O)C$_{2-10}$alkynylC(O)R$_{11}$, —C(O)C$_{1-10}$alkylCH(OR$_{11}$)(OR$_{11}$), —C(O)C$_{2-10}$alkenylCH(OR$_{11}$)(OR$_{11}$), —C(O)C$_{2-10}$alkynylCH(OR$_{11}$)(OR$_{11}$), —C(O)C$_{1-10}$alkylSR$_{11}$, —C(O)C$_{2-10}$-alkenylSR$_{11}$, —C(O)C$_{2-10}$alkynylSR$_{11}$, —C(O)C$_{1-10}$alkylC(O)OR$_{11}$, —C(O)C$_{2-10}$alkenylC(O)OR$_{11}$, —C(O)C$_{2-10}$alkynylC(O)OR$_{11}$, —C(O)C$_{1-10}$alkylC(O)SR$_{11}$, —C(O)C$_{2-10}$alkenylC(O)SR$_{11}$, —C(O)C$_{2-10}$alkynylC(O)SR$_{11}$, R$_{10}$ is —C$_{1-6}$alkyl, —C$_{2-6}$alkenyl, —C$_{2-6}$alkynyl, —C(O)C$_{1-6}$alkyl, —C(O)C$_{2-6}$alkenyl, C(O)C$_{2-6}$alkynyl, —C(O)aryl, —C(O)C$_{1-6}$alkylaryl, —C(O)C$_{2-6}$alkenylaryl, —C(O)C$_{2-6}$alkynylaryl; and
R$_{11}$ is hydrogen, —C$_{1-10}$alkyl, —C$_{2-10}$ alkenyl, —C$_{2-10}$alkynyl, cycloalkyl or aryl; wherein each alkyl, alkenyl, alkynyl, cycloalkyl or aryl group is optionally substituted.

In some embodiments, the epoxytiglienone compound of formula (I) is a compound of formula (II):

(II)

or a geometric isomer or stereoisomer or a pharmaceutically acceptable salt thereof; where R$_6$, R$_7$ and R$_9$ are as defined for formula (I).

In some embodiments of formulae (I) and (II), the alkyl or alkenyl group of R$_2$ and/or R$_3$ or R$_9$ are branched alkyl or alkenyl groups.

In some embodiments, the alkyl or alkenyl group of R$_2$ and/or R$_3$ or R$_9$ has a chain length of intermediate hydrophobicity, for example, C4, C5 or C6.

In some embodiments, the C20 hydroxy group is substituted with an acyl group (R$_6$), for example an acetyl (—C(O)CH$_3$), —C(O)CH$_2$CH$_3$, —C(O)CH(CH$_3$)$_2$ or —C(O)CH$_2$CH$_2$CH$_3$.

In some embodiments, the alkyl, alkenyl, alkynyl, cycloalkyl or aryl groups are optionally substituted by a halo group selected from fluoro, chloro, bromo and iodo, especially fluoro and chloro. In some embodiments the alkyl, alkenyl, alkynyl, cycloalkyl or aryl groups of the esters at R$^9$ and R$^{10}$ are optionally substituted by a halo group selected from fluoro, chloro, bromo and iodo, especially fluoro and chloro.

In particular embodiments of formulae (I) or (II), one or more of the following applies:
R$_1$ is —C$_{1-3}$alkyl, especially —CH$_3$;
R$_2$ is —OC(O)C$_{1-20}$alkyl, —OC(O)C$_{2-20}$alkenyl, —OC(O)C$_{2-20}$alkynyl, —OC(O)cycloalkyl, —OC(O)C$_{1-10}$alkylcycloalkyl; —OC(O)C$_{2-10}$alkenylcycloalkyl, —OC(O)C$_{2-10}$alkynylcycloalkyl, —OC(O)aryl, —OC(O)C$_{1-10}$alkylaryl, —OC(O)C$_{2-10}$alkenylaryl, —OC(O)C$_{2-10}$alkynylaryl, —OC(O)C$_{1-10}$alkylC(O)R$_{11}$, —OC(O)C$_{2-10}$alkenylC(O)R$_{11}$, —OC(O)C$_{2-10}$alkynylC(O)R$_{11}$, —OC(O)C$_{1-10}$alkylCH(OR$_{11}$)(OR$_{11}$), —OC(O)C$_{2-10}$alkenylCH(OR$_{11}$)(OR$_{11}$), —OC(O)C$_{2-10}$alkynylCH(OR$_{11}$)(OR$_{11}$), —OC(O)C$_{1-10}$alkylSR$_{11}$, —OC(O)C$_{2-10}$alkenylSR$_{11}$, —OC(O)C$_{2-10}$alkynylSR$_{11}$, —OC(O)C$_{1-10}$alkylC(O)OR$_{11}$, —OC(O)C$_{2-10}$alkenylC(O)OR$_{11}$, —OC(O)C$_{2-10}$alkynylC(O)OR$_{11}$, —OC(O)C$_{1-10}$alkylC(O)SR$_{11}$, —OC(O)C$_{2-10}$alkenylC(O)SR$_{11}$ or —OC(O)C$_{2-10}$alkynylC(O)SR$_{11}$; especially —OC(O)C$_{1-10}$alkyl, —OC(O)C$_{2-10}$alkenyl, —OC(O)C$_{2-10}$alkynyl, —OC(O)cycloalkyl, —OC(O)C$_{1-10}$alkylcycloalkyl; —OC(O)C$_{2-10}$alkenylcycloalkyl, —OC(O)C$_{2-10}$alkynylcycloalkyl or —OC(O)aryl; more especially —OC(O)C$_{1-6}$alkyl, —OC(O)C$_{2-6}$alkenyl or —OC(O)C$_{2-6}$alkynyl or —OC(O)C$_{4-6}$alkyl, —OC(O)C$_{4-6}$alkenyl or —OC(O)C$_{4-6}$alkynyl;
R$_3$ is —OC(O)C$_{1-20}$alkyl, —OC(O)C$_{2-20}$alkenyl, —OC(O)C$_{2-20}$alkynyl, —OC(O)cycloalkyl, —OC(O)C$_{1-10}$alkylcycloalkyl; —OC(O)C$_{2-10}$alkenylcycloalkyl, —OC(O)C$_{2-10}$alkynylcycloalkyl, —OC(O)aryl, —OC(O)C$_{1-10}$alkylaryl, —OC(O)C$_{2-10}$alkenylaryl, —OC(O)C$_{2-10}$alkynylaryl, —OC(O)C$_{1-10}$alkylC(O)R$_{11}$, —OC(O)C$_{2-10}$alkenylC(O)R$_{11}$, —OC(O)C$_{2-10}$alkynylarylC(O)R$_{11}$, —OC(O)C$_{1-10}$alkylCH(OR$_{11}$)(OR$_{11}$), —OC(O)C$_{2-10}$alkenylCH(OR$_{11}$)(OR$_{11}$), —OC(O)C$_{2-10}$alkynylCH(OR$_{11}$)(OR$_{11}$), —OC(O)C$_{1-10}$alkylSR$_{11}$, —OC(O)C$_{2-10}$alkenylSR$_{11}$, —OC(O)C$_{2-10}$alkynylSR$_{11}$, —OC(O)C$_{1-10}$alkylC(O)OR$_{11}$, —OC(O)C$_{2-10}$alkenylC(O)OR$_{11}$, —OC(O)C$_{2-10}$alkynylC(O)OR$_{11}$, —OC(O)C$_{1-10}$alkylC(O)SR$_{11}$, —OC(O)C$_{2-10}$alkenylC(O)SR$_{11}$ or —OC(O)C$_{2-10}$alkynylC(O)SR$_{11}$; especially —OC(O)C$_{1-10}$alkyl, —OC(O)C$_{2-10}$alkenyl, —OC(O)C$_{2-10}$alkynyl, —OC(O)cycloalkyl, —OC(O)C$_{1-10}$alkylcycloalkyl; —OC(O)C$_{2-10}$alkenylcycloalkyl, —OC(O)C$_{2-10}$alkynylcycloalkyl or —OC(O)aryl; more especially —OC(O)C$_{1-6}$alkyl, —OC(O)C$_{2-6}$alkenyl or —OC(O)C$_{2-6}$alkynyl or —OC(O)C$_{2-6}$alkynyl or —OC(O)C$_{4-6}$alkyl, —OC(O)C$_{4-6}$alkenyl or —OC(O)C$_{4-6}$alkynyl;
R$_4$ and R$_5$ are independently selected from —C$_{1-3}$alkyl, especially —CH$_3$;
R$_6$ is hydrogen, —C(O)C$_{1-6}$alkyl, —C(O)C$_{2-6}$alkenyl, —C(O)C$_{2-6}$alkynyl or —C(O)aryl; especially hydrogen, —C(O)C$_{1-3}$alkyl, —C(O)C$_{2-3}$alkenyl or —C(O)C$_{2-3}$alkynyl, more especially hydrogen or —C(O)CH$_3$;

R<sub>7</sub> is hydroxyl, —OC(O)C$_{1-6}$alkyl, —OC(O)C$_{2-6}$alkenyl or —OC(O)C$_{2-6}$alkynyl, especially hydroxyl, —OC(O)C$_{1-3}$alkyl, —OC(O)C$_{2-3}$alkenyl or —OC(O)C$_{2-3}$alkynyl, more especially hydroxyl or —OC(O)CH$_3$; and R$_8$ is —C$_{1-3}$alkyl, especially —CH$_3$.

In some embodiments, the compounds of formulae (I) and/or (II) have stereochemistry as shown in formula (III) below:

(III)

In some embodiments, the epoxide in the 6,7-position is above the plane of the ring system. In other embodiments, the epoxide in the 6,7-position is below the plane of the ring system. In some embodiments, the R$_2$ group in the 12 position is S and in other embodiments, the R$_2$ group in the 12 position is R.

In particular embodiments the epoxytiglienone compound is selected from:

12-tigloyl-13-(2-methylbutanoyl)-6,7-epoxy-4,5,9,12,13,20-hexahydroxy-1-tiglien-3-one (Compound 1);

12,13-di-(2-methylbutanoyl)-6,7-epoxy-4,5,9,12,13,20-hexahydroxy-1-tiglien-3-one (Compound 2);

12-hexanoyl-13-(2-methylbutanoyl)-6,7-epoxy-4,5,9,12,13,20-hexahydroxy-1-tiglien-3-one (Compound 3);

12,13-dihexanoyl-6,7-epoxy-4,5,9,12,13,20-hexahydroxy-1-tiglien-3-one (Compound 4);

12-myristoyl-13-(2-methylbutanoyl)-6,7-epoxy-4,5,9,12,13,20-hexahydroxy-1-tiglien-3-one (Compound 5);

12-tigloyl-13-(2-methylbutanoyl)-6,7-epoxy-4,5,9,12,13-pentahydroxy-20-acetyloxy-1-tiglien-3-one (Compound 6);

12-myristoyl-13-acetyloxy-6,7-epoxy-4,5,9,12,13,20-hexahydroxy-1-tiglien-3-one (Compound 7);

12-propanoyl-13-(2-methylbutanoyl)-6,7-epoxy-4,5,9,12,13,20-hexahydroxy-1-tiglien-3-one (Compound 8);

12,13-ditigloyl-6,7-epoxy-4,5,9,12,13,20-hexahydroxy-1-tiglien-3-one (Compound 9);

12-(2-methylbutanoyl)-13-tigloyl-6,7-epoxy-4,5,9,12,13,20-hexahydroxy-1-tiglien-3-one (Compound 10);

12-butanoyl-13-(2-methylbutanoyl)-6,7-epoxy-4,5,9,12,13,20-hexahydroxy-1-tiglien-3-one (Compound 11);

12-(3,3-dimethylbut-2-enoyl)-13-(2-methylbutanoyl)-6,7-epoxy-4,5,9,12,13,20-hexahydroxy-1-tiglien-3-one (Compound 12);

12-hex-2,4-dienoyl-13-(2-methylbutanoyl)-6,7-epoxy-4,5,9,12,13,20-hexahydroxy-1-tiglien-3-one (Compound 13);

12-tigloyl-13-(2-methylpropanoyl)-6,7-epoxy-4,5,9,12,13,20-hexahydroxy-1-tiglien-3-one (Compound 14);

12-but-2-enoyl-13-(2-methylbutanoyl)-6,7-epoxy-4,5,9,12,13,20-hexahydroxy-1-tiglien-3-one (Compound 15);

12-tigloyl-13-butanoyl-6,7-epoxy-4,5,9,12,13,20-hexahydroxy-1-tiglien-3-one (Compound 16);

12,13-dibutanoyl-6,7-epoxy-4,5,9,12,13,20-hexahydroxy-1-tiglien-3-one (Compound 17);

12,13-dipentanoyl-6,7-epoxy-4,5,9,12,13,20-hexahydroxy-1-tiglien-3-one (Compound 18);

12,13-di-(2E,4E)-hexa-2,4-dienoyl-6,7-epoxy-4,5,9,12,13,20-hexahydroxy-1-tiglien-3-one (Compound 19);

12,13-di-(2-methylbutanoyl)-6,7-epoxy-4,5,9,12,13,20-hexahydroxy-1-tiglien-3-one (Compound 20);

12-(2-methylprop-2-enoyl)-13-(2-methylbutanoyl)-6,7-epoxy-4,5,9,12,13,20-hexahydroxy-1-tigliaen-3-one (Compound 21);

12-(3-butenoyl)-13-nonanoyl-6,7-epoxy-4,5,9,12,13,20-hexahydroxy-1-tigliaen-3-one (Compound 22);

12,13-di-nonanoyl-6,7-epoxy-4,5,9,12,13,20-hexahydroxy-1-tigliaen-3-one (Compound 23);

12,13-di-heptanoyl-6,7-epoxy-4,5,9,12,13,20-hexahydroxy-1-tigliaen-3-one (Compound 24);

12,13-di-(3-methylbutanoyl)-6,7-epoxy-4,5,9,12,13,20-hexahydroxy-1-tigliaen-3-one (Compound 25); or a pharmaceutically acceptable salt thereof.

In particular embodiments, the 6,7-eopoxytiglienone compound is selected from compounds 1, 2, 3, 4, 6, 8, 9, 10, 11, 12, 13, 14, 15, 16, 17, 18, 19, 20, 21 and 25, especially compounds 1, 2, 6, 8, 9, 10, 11, 14, 15, 16, 17, 18, 20 and 25.

Compositions

While the 6,7-epoxytiglienone compounds or pharmaceutically acceptable salts thereof may be administered neat, it may be more convenient to administer them in the form of a pharmaceutical composition, together with a pharmaceutically acceptable carrier, diluent and/or excipient.

Dosage form and rates for pharmaceutical use and compositions are readily determinable by a person of skill in the art.

The 6,7-epoxytiglienone compound is formulated for localized administration directly onto or into the tumour being treated. In some embodiments, the 6,7-epoxytiglienone compound is formulated for topical administration in the form of a gel, ointment, lotion, cream or transdermal patch that may be applied directly onto the tumour being treated. In other embodiments, the epoxytiglianone compound is formulated for injection, especially intratumoural injection where the compound is injected into one or more places in a tumour.

Suitably, the pharmaceutical composition(s) comprise a pharmaceutically acceptable excipient or an acceptable excipient. By "pharmaceutically acceptable excipient" is meant a solid or liquid filler, diluent or encapsulating substance that may be safely used. Depending upon the particular route of administration, a variety of carriers, well known in the art may be used. These carriers or excipients may be selected from a group including sugars, starches, cellulose and its derivatives, cyclodextrins, malt, gelatine or other gelling agents, polymers, talc, calcium sulphate, vegetable oils, synthetic oils, alcohols and/or polyols, alginic acid, phosphate buffered solutions, emulsifiers, isotonic saline, and pyrogen-free water.

Liquid form preparations include solutions, suspensions, and emulsions, for example, water or water-propylene glycol solutions. For example, injectable liquid preparations can be formulated as solutions in aqueous 1,2-propanediol, dimethylsulfoxide (DMSO), aqueous solutions of gamma cyclodextrin or 2-hydroxypropyl-beta-cyclodextrin, saline solution or polyethylene glycol solution, with or without buffer. A preferred range of pH is 3.0-4.5. Suitable buffers buffer the preparation at pH 3.5-4.5 and include, but are not limited to, acetate buffer and citrate buffer.

The compositions of 6,7-epoxytiglienone compound may thus be formulated for parenteral administration (e.g. by injection, for example bolus injection) and may be presented in unit dose form in ampoules, pre-filled syringes, small volume infusion or in multi-dose containers with an added preservative. The compositions may take such forms as suspensions, solutions, gels or emulsions in oily or aqueous vehicles, and may contain formulatory agents such as suspending, stabilising and/or dispersing agents.

Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical compositions of 6,7-epoxytiglienone compound suitable for administration may be presented in discrete units such as syringes, vials, tubes or sachets each containing a predetermined amount of one or more pharmaceutically active 6,7-epoxytiglienone compounds, as a powder or granules or as a solution or a suspension in an aqueous liquid, a cyclodextrin solution, a non-aqueous liquid, an oil-in-water emulsion or a water-in-oil emulsion or as a solution or suspension in a cream or gel or as a suspension of micro- or nano-particles incorporating a 6,7-epoxytiglienone compound, including but not limited to silica or polylactide micro- or nano-particles. Such compositions may be prepared by any of the methods of pharmacy but all methods include the step of bringing into association one or more pharmaceutically active compounds of the invention with the carrier which constitutes one or more necessary ingredients. In general, the compositions are prepared by uniformly and intimately admixing the agents of the invention with liquid carriers or finely divided solid carriers or both, and then, if necessary, shaping the product in to the desired presentation.

For topical administration to the epidermis or other organ, the compounds according to the invention may be formulated as gels, ointments, emulsions, pastes, creams or lotions, or as a transdermal patch. Gels may be prepared using suitable thickening agents and adding them to aqueous/alcoholic compositions of compound. Suitable thickening or gelling agents are known in the art, such as the polyvinyl carboxy polymer Carbomer 940. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration also include solutions or suspensions that may be administered topically in the form of a bath or soak solution or a spray or may be absorbed into a dressing.

EXAMPLES

Example 1: Abscopal (Anenestic) Effects of Compound 1 in Two Human Melanoma Patients A Phase I, open-label, multicentre, dose-escalation study of intratumoural Compound 1 in patients with accessible cutaneous, subcutaneous or nodal tumours refractory to conventional therapy was conducted (Panizza et al. 2019). Patients received Compound 1 via direct bolus injection(s) into no more than 3 selected superficial tumours on Day 1. The volume of the solution was determined by body surface area (BSA) using the formula Volume=(BSA×Dose Level)/Concentration of Drug, where Volume is in mL, BSA is in $m^2$, Dose Level is in $mg/m^2$, and Concentration of Drug is in mg/mL. The solution was injected into a volume of tumour estimated to be twice the volume of the injected solution (e.g., 1 mL Compound 1 into 2 $cm^3$ of tumour). Where tumours were larger than that required for the dose, a section of the tumour was injected. When multiple tumours were treated, the dose was divided in proportion to the target volume of each tumour. The dose was administered using a minimal number of injections in a fanning manner to spread the dose evenly throughout the bulk of the tumour. After assessments for follow-up on Days 3, 5, 8, 15, and 22 and, if wound healing or stabilisation did not occur by Day 22, every 7 days thereafter until full healing or stabilisation was achieved.

Of the patients recruited into this trial, two had metastatic melanoma, with an abscopal effect observed in both patients subsequent to intratumoural treatment with Compound 1 as a monotherapy.

Patient 1 had originally been diagnosed with melanoma in August 2011 and a local tumour mass was removed surgically. Subsequent surgery in November 2015 removed a metastatic tumour from the left axilla. The patient had no radiotherapy, chemotherapy or other interventions during the course of their treatment of this disease. In January 2016 the patient had developed more extensive axillary nodal metastatic melanoma while fine needle aspiration (FNA) confirmed more widespread disease with a contralateral parotid nodal melanoma mass and a clinically suspicious leg tumour. At this time Compound 1 was administered to two new tumours in the left axilla. There was a Complete Response (using RECIST v1.1 criteria; Eisenhauer et al. 2009) with resolution of both tumours to which the drug was administered. Significantly, the untreated parotid mass and the leg mass also resolved following treatment with Compound 1 and this patient remained disease free for 33 months following treatment but subsequently developed widespread metastatic disease, although axillary and parotid nodes remained clear. The details of this patient and treatment are set out in Table 1.

TABLE 1

Patient 1

| Cancer type and disease stage | Locations and number of treated tumours | Volume of treated tumour | Response in the treated tumour[1] | Location of non-target tumours | Response at non-target tumour[1] | Disease free status |
|---|---|---|---|---|---|---|
| Melanoma Stage III | Axilla (2) | 1 $cm^3$ | Complete response | Contralateral parotid node | Complete | Patient remained clinically and radiologically clear of |
| | | | | Knee | Complete | |

TABLE 1-continued

| Patient 1 | | | | | | |
|---|---|---|---|---|---|---|
| Cancer type and disease stage | Locations and number of treated tumours | Volume of treated tumour | Response in the treated tumour[1] | Location of non-target tumours | Response at non-target tumour[1] | Disease free status |
| | | | | | | disease at 33 months but subsequently developed progressive disease |

[1]Response category based on RECIST v1.1 criteria, Eisenhauer et al. 2009

At the time of treatment with Compound 1 Patient 2 had melanoma (Grade IV) with dermal, nodal and pleural metastases. This patient had been initially diagnosed with melanoma in February 2015 and had surgery to remove tumours on three occasions between February 2015 and March 2016. A course of radiotherapy for chest wall metastases followed in June 2016 resulting a partial local response to radiation therapy. Progressive disease soon developed and was unresponsive despite receiving four doses of pembrolizumab. After a two month 'wash-out' period following these previous therapies, the patient had three cutaneous melanoma metastases on the right upper extremity treated with intra-tumourally-administered Compound 1. There was Complete Response (RECIST v1.1) with all three tumours to which the drug had been administered fully resolving. Significantly, a fourth cutaneous tumour, which was not injected with study drug underwent an abscopal (anenestic) response and completely resolved macroscopically during follow-up. Approximately 4 weeks after injection of the upper extremity tumours with Compound 1, a superficial sternal tumour (containing biopsy-proven metastatic melanoma) was injected, which also showed a complete response. Of note, CT scans showed abscopal (anenestic) responses in non-injected lymph node and pleural tumours, with complete resolution of a 24-mm left axillary node and a 29-mm right pleural nodule, and a reduction in size of a right inguinal node. The patient remained well and off treatment until a CT scan, performed 14 months after the second Compound 1 injection, revealed progressive tumour involving bone and lymph nodes. The details of this patient are shown in Table 2.

TABLE 2

| Patient 2 | | | | | | |
|---|---|---|---|---|---|---|
| Cancer type and disease stage | Locations and number of treated tumours | Volume of tumour | Response in the treated tumour[1] | Location of non-target treated tumours | Response at non-target tumour[1] | Disease free status |
| Melanoma Stage IV (BRAF wild type) | Arm (3) | 1.3 cm³ | Complete response | Contralateral parotid node | Complete | Progressive disease identified from CT scan at 14 months involving bone and lymph nodes |
| | Sternum (1) | 1.1 cm³ | Complete response | Arm (satellite metastasis) | Complete | |
| | | | | Left axillary lymph node (24 mm) | Complete | |
| | | | | Right pleural nodule (29 mm) | Complete | |
| | | | | Right inguinal lymph node | Partial | |

[1]Response category based on RECIST v1.1 criteria, Eisenhauer et al. 2009

Example 2: Abscopal Effects of Compound 1 in Five Types of Canine Cancer a) Spontaneously-Arising Cancers in Dogs are Recognised as a Reliable Model of Many Cancers in Humans Naturally-occurring cancers in dogs have striking biological similarities to cancers in humans and there is a substantial recent body of scientific literature demonstrating the value of canine cancers both as 'real-world' models of human disease and for predicting responses to new cancer therapies (Gardner et al. 2016). For example, important clinically-relevant features that canine cancers share with human cancers include that they:

Are often relatively large tumours that develop spontaneously in large outbred mammals with a background of genetic diversity similar to that in the human population;

Are genetically complex tumours that develop over long periods of time and exist in the presence of an intact immune system where there are complex interactions between the host immune system and cancer cells which shape tumour development and progression;

Have similar molecular and anatomical features;

Have significant tumour heterogeneity both within patients and between patients;

Recur and metastasise to the same sites as similar tumour types in humans; and,

Develop resistance if exposed to repeated courses of therapeutics.

Examples of canine cancers for which there is published scientific literature demonstrating their direct relevance as models for human disease include melanomas, squamous cell carcinomas, breast cancers, lymphomas, soft tissue sarcomas, invasive urinary bladder cancers, gliomas and osteosarcomas.

b) Observations of Abscopal Effect in Five Cancer Types in Canine Clinical Cases Studies Following Locally Administered Epoxytiglienone The prototype epoxytiglienone Compound 1 is currently in late stage clinical development as a locally administered treatment for mastocytomas in dogs (Miller et al. 2019). In parallel, the efficacy of the compound is also being evaluated in a series of case studies across a broader range of cutaneous and subcutaneous canine cancer types. The majority of these clinical cases involved treatment of non-systemic disease where only one tumour was present on each patient. However, in a number of cases, patients had systemic multifocal disease and in these instances the compound was administered to a subset of the tumours present with the aim of local palliation only. Abscopal effects in non-adjacent, untreated tumours were subsequently observed in eight patients with multi-focal disease from these cases. The five tumour types in which abscopal effects were observed were mastocytoma (mast cell tumours), histiolytic sarcoma (a neoplasm of haematopoietic origin), cutaneous squamous cell carcinoma (arising from solar keratoses), basal cell carcinoma, mixed fields of cutaneous squamous cell carcinoma and haemangiosarcoma (arising from solar keratoses), and haemangiosarcoma (Table 3).

A consistent treatment protocol was used in all case studies of locally-administered epoxytiglienones as follows. All dogs were client owned animals and informed consent was obtained from owners prior to patient enrolment and treatment. Biopsies were taken 7 to 14 days prior to treatment to determine tumour type except in the case of mastocytomas where confirmation of tumour type was based on cytology obtained from fine needle aspirates of the tumour mass. At the time of treatment, the target tumour(s) to which the drug was to be administered were measured. The dose to be administered intratumourally to each tumour was then calculated on the basis of tumour volume at a rate of between 0.1 mg to 0.5 mg of 6,7-epoxytiglienone per cubic centimetre of tumour volume. In cases of multifocal disease where a single tumour or a small number of the tumours present were targeted for palliation only purposes, other visible and palpable tumours on the patient were counted where possible. Treatment of the target tumours involved a single injection of the epoxytiglienone into each tumour. Photographs of the target tumours were taken immediately prior to treatment and over the course of their treatment response. The target tumours were evaluated regularly over a 28 day period and the final outcome of treatment categorised as Complete Response (full resolution of the target tumour), Partial Response (some tumour tissue still present at 28 days) or Poor Response (significant tumour mass still present). Veterinarians noted that response in the non-target tumours that had an abscopal effect was characterised by a shrinkage and disappearance of these tumours, sometimes associated with a transient slight darkening of the skin. This contrasted with the very distinctive haemorrhagic necrosis and tumour slough that was characteristic of epoxytiglienones when they are injected directly into target tumours.

TABLE 3

| Patient ID | Cancer type | Treatment history | Location (number) of treated tumours | Response in treated tumour | Location and number of untreated tumours | Response untreated | Time to abscopal response (days) | Re-occurrence of abscopal tumours/disease free status |
|---|---|---|---|---|---|---|---|---|
| C-JN | Histiolytic sarcoma | Nil | Left Shoulder (2) | Complete | Left Shoulder (6 satellite tumours) | Complete | 7 to 14 days | No re-occurrence after 6 months |
| | | | Right hind leg medial (2) | Complete | Right hind leg medial (3 satellite tumours) | Complete | 7 to 14 days | (euthanased for unrelated morbidity) |
| | | | Right hind leg axilla (2) | Complete | | | | |
| | | | | | Back of neck (7) | Complete | 7 to 14 days | |
| | | | | | Right flank (5) | Complete | | |
| C-IS | Cutaneous squamous cell carcinoma | Surgery | Abdominal (7) | Complete | Abdominal (>20 satellite tumours) | Complete | 7 to 14 days | No re-occurrence after 4 months |
| C-LW | Mixed fields of cutaneous squamous cell carcinoma/ haemangio- sarcoma* | Surgery, numerous occasions | Abdominal (6), 3 discrete treatment fields | Complete | Abdominal (>15 satellite tumours) | Complete | 7 to 14 days | No re-occurrence of treated fields. New tumours developed from new areas of differentiating solar keratoses at 3 months |
| C-MC | Haemangio- sarcoma | Nil | Inner right thigh (1) | Complete | Right inguinal lymph node (1) | Complete | 14 days | No re-occurrence after 36 months |
| C-RC | Basal cell carcinoma | Surgery (6 months previously) | Left front hock (1) | Complete | Front left shoulder | Complete | 7 to 14 days | No re-occurrence after 20 months |
| | | | Right rear hock (1) | Complete | Right rear thigh | Complete | 7 to 14 days | |
| CM-02 | Mastocytoma | Nil | Left caudal thigh (1) | Complete | Cranial aspect of thigh (right hind leg) | Complete | 21 to 28 days | No re-occurrence after 3 months |
| CD-01 | Mastocytoma | Nil | Near vulva | Complete | Medial aspect of proximal left front leg | Complete | 7 days | No re-occurrence after 3 months |
| | | | | | Caudolateral aspect of thigh on right hind leg | Complete | 14 days | No re-occurrence after 3 months |

TABLE 3-continued

| Patient ID | Cancer type | Treatment history | Location (number) of treated tumours | Response in treated tumour | Location and number of untreated tumours | Response untreated | Time to abscopal response (days) | Re-occurrence of abscopal tumours/disease free status |
|---|---|---|---|---|---|---|---|---|
| CD-02 | Mastocytoma | Nil | Right flank-cranial | Complete | Left flank-cranial | Complete | 7 days | No re-occurrence after 3 months |

*arising from solar keratoses

Example 3: Abscopal Effect of Compound 1 in Immunocompetent Murine Cancer Models A in vivo study using sub-optimal doses of Compound 1 investigated abscopal effects in immunocompetent C57BL/6 mice. The C57BL/6 mouse strain was selected as it is widely used in studying the ability of novel agents to induce abscopal effects, especially relating to shrinkage of untreated tumours that occurs concurrently with, or soon after, shrinkage of treated targeted tumours.

B16-F10 (melanoma) or Panc02 (pancreatic) tumours (2 per mouse, 5 mice per treatment group) were grown subcutaneously on immunocompetent mice (C57BL/6) to a size of 75-100 mm$^3$, after which a single tumour was injected intratumourally with either vehicle alone (50 µL, 40% propylene glycol (PG), 30 mM sodium acetate pH 4.3) or vehicle containing 7.5 µg Compound 1 to determine if Compound 1 administration alone can promote the development of abscopal effects in different cancer subtypes. The murine cancer cell lines were previously transduced with lentivirus expressing luciferase prior to injection to visualize both primary tumour burden and possible metastases using bioluminescent imaging. All mice were monitored according to procedures approved by the QIMR Berghofer Medical Research Institute Animal Ethics Committee for this study.

Figure 1A:
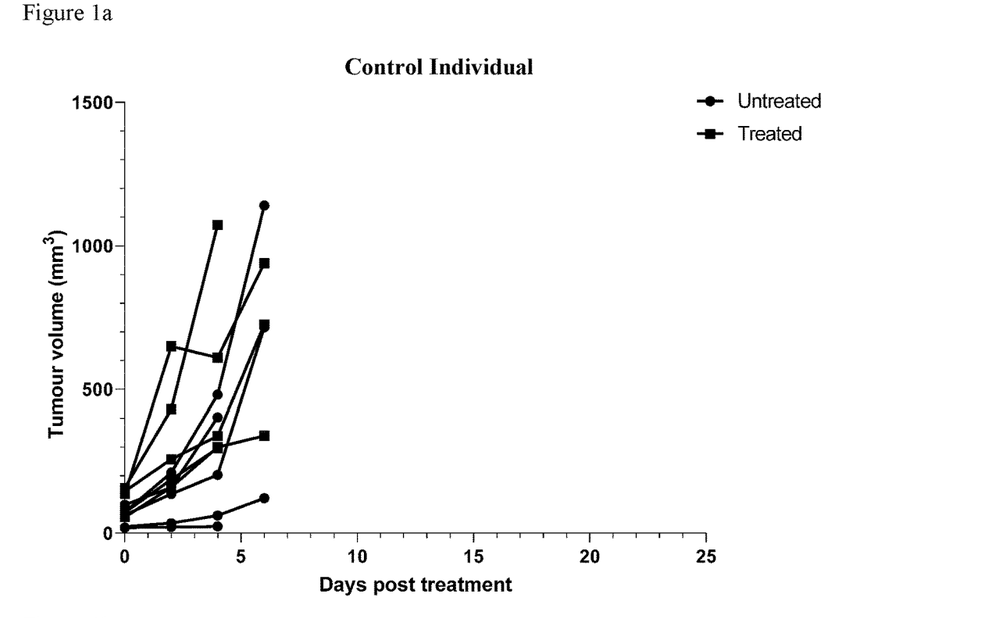
Figure 1B:
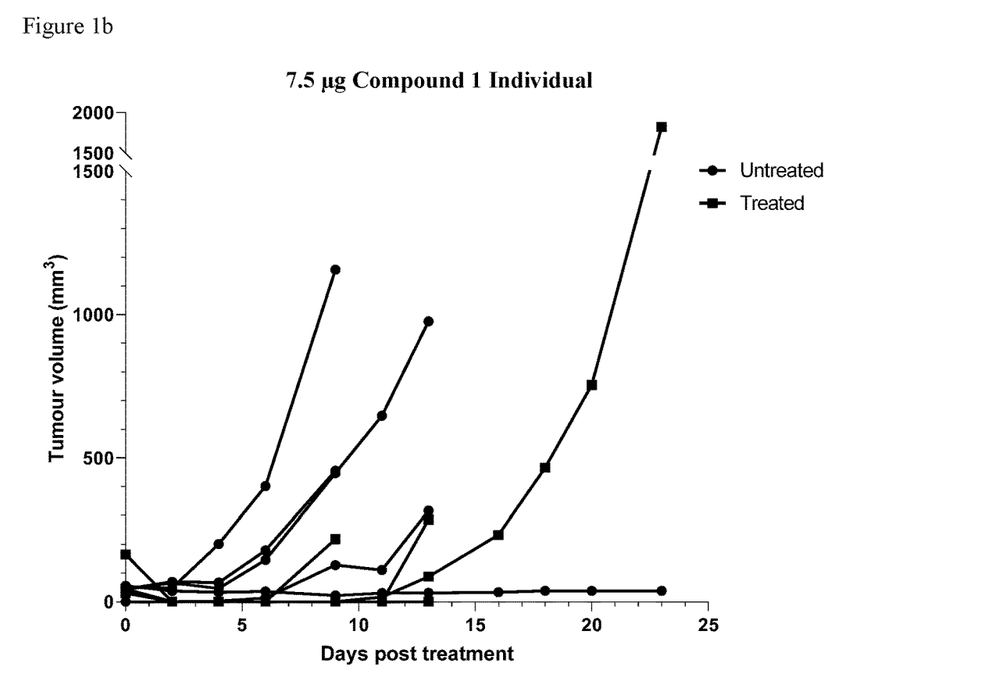
Figure 2A:
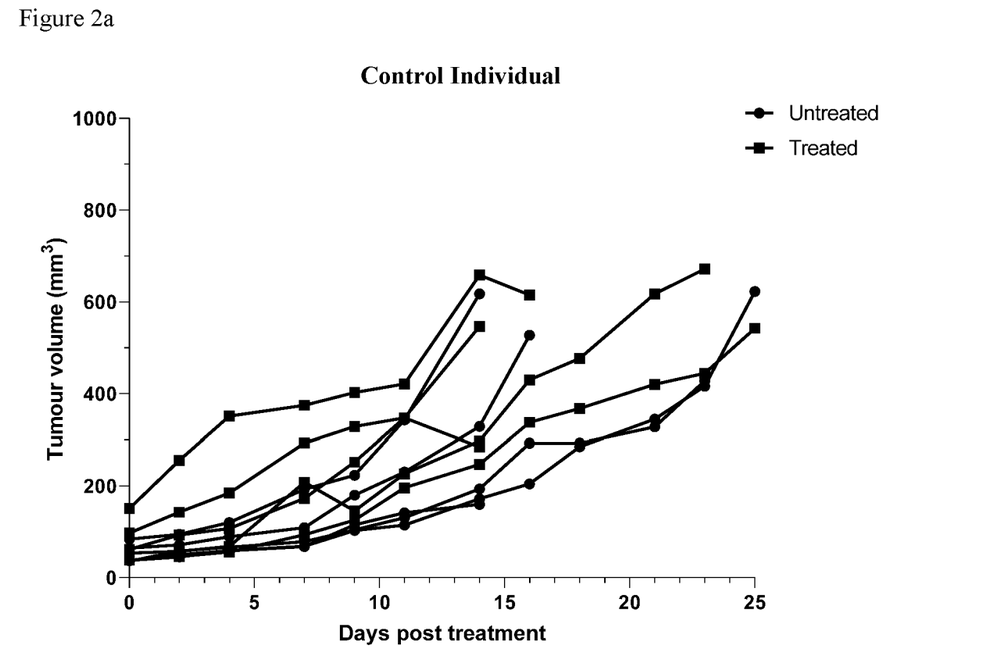
Figure 2B:
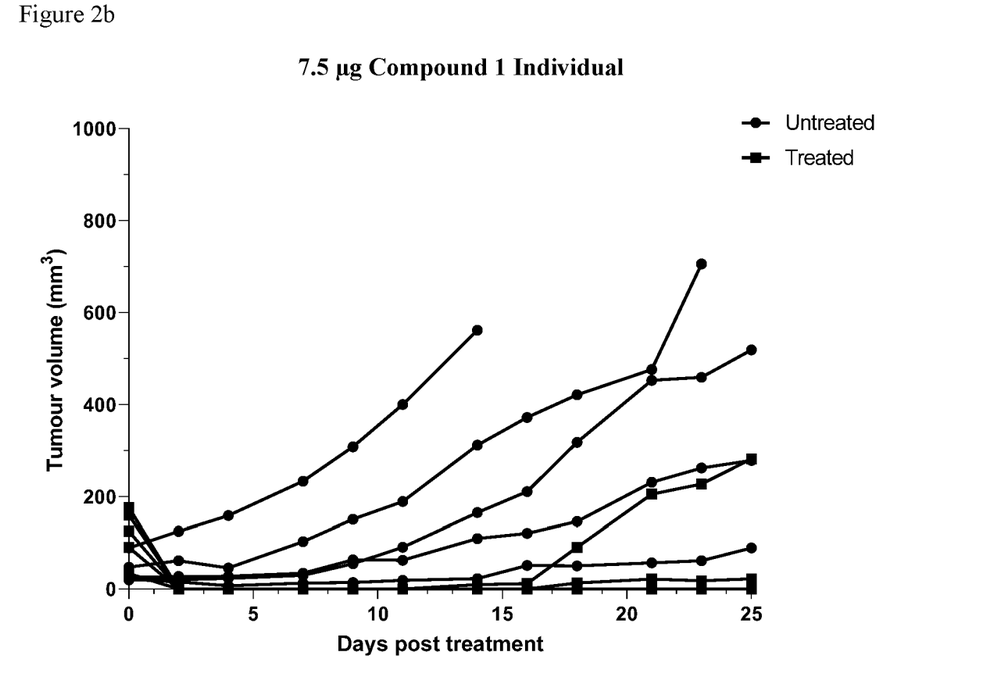

The results are shown in FIGS. 1 (B16-F10) and 2 (Panc02). The results show that treatment with the vehicle alone to one tumour did not have a significant effect on growth of the untreated tumour. In contrast, treatment with a sub-efficacious (7.5 µg) dose of Compound 1 led to reduction of tumour growth in the treated tumour. In addition untreated adjacent tumours also showed a response to the Compound 1 therapy that was not observed with vehicle alone.

REFERENCES

Abuodeh Y, Venkat P & Kim S (2016). Systematic review of case reports on the abscopal effect. *Current Problems in Cancer* 40: 25-37.

Adams J L, Smothers J, Srinivasan R & Hoos A (2015). Big opportunities for small molecules in immuno-oncology. *Nature Reviews Drug Discovery* 14: 603-622.

Aznar M A, Tinari N, Rullan A J et al. (2016). Intratumoral delivery of immunotherapy act locally, think globally. *Journal of Immunology* 198: 32-39.

Barnett C M E, Broit N, Yap P Y et al. (2019). Optimising intratumoral treatment of head and neck squamous cell carcinoma models with the diterpene ester Tigilanol tiglate. *Investigational New Drugs* 37: 1-8.

Boutros C, Tarhini A, Routier O et al. (2016). Safety profiles of anti-CTLA-4 and anti-PD-1 antibodies. *Nature Reviews Clinical Oncology* 13: 473-486.

Boyle G M, D'Souza M M, Pierce C J et al. (2014). Intra-lesional injection of the novel PKC activator EBC-46 rapidly ablates tumors in mouse models. *PLoS One* 9(10): e108887.

Chalmers Z R, Connelly C F, Fabrizio D et al. (2017). Analysis of 100,000 human cancer genomes reveals the landscape of tumor mutational burden. *Genome Medicine* 9(1): 34

Demaria S, Ng B, Devitt M L et al. (2004). Ionizing radiation inhibition of distant untreated tumors (abscopal effect) is immune mediated. *International Journal of Radiation Oncology Biology Physics* 58: 862-870.

Eisenhauer E A, Therasse P, Bogaerts J et al. (2009). New response criteria in solid tumours: revised RECIST guideline (version 1.1). *European Journal of Cancer* 45: 228-247.

Gardner et al. 2016. Dogs as a model for cancer. *Annual Review of Animal Biosciences* 4: 199-222.

Gibney G T, Weiner L M & Atkins M B (2016). Predictive biomarkers for checkpoint inhibitor-based immunotherapy. *Lancet Oncology* 16: e542-551.

Goodman A M, Kato S, Bazhenova L et al. (2017). Tumor mutational burden as an independent predictor of response to immunotherapy in diverse cancers. *Molecular Cancer Therapeutics* 16: 2598-2608

Hammerich L, Binder A & Brody J D (2015). In situ vaccination: cancer immunotherapy both personalized and off the shelf. *Molecular Oncology* 9: 1966-1981.

Marabelle A, Tselikas L, de Baere T & Houot R (2017). Intratumoral immunotherapy: using the tumor as the remedy. *Annals of Oncology* 28: xii33-xi43.

Marabelle A, Andtbacka R, Harrington K, et al. (2018). Starting the fight in the tumor: expert recommendations for the development of human intratumoral immunotherapy (HIT-IT). *Annals of Oncology* 29: 2163-2174.

Mastrangelo M J, Bellet R E, Berkelhammer J et al. (1975). Regression of pulmonary metastatic disease associated with intralesional BCG therapy of intracutaneous melanoma metastases. *Cancer* 36: 1305-1308.

Marin-Acevedo J A, Dholaria B, Soyano A E et al. (2018). Next generation of immune checkpoint therapy in cancer: new developments and challenges. *Journal of Hematology & Oncology* 11: 39.

Melendez B, et al., (2018). Methods of measurement for tumor mutational burden in tumor tissue. *Translational Lung Cancer Research* 7(6):661-667.

Miller J, Campbell J, Blum A et al. (2019). Dose characterization of the investigational anticancer drug tigilanol tiglate (EBC-46) in the local treatment of canine mast cell tumors. *Frontiers in Veterinary Science* 2019.00106.

Panizza B J, de Souza P, Cooper A, Roohullah A, Karapetis C S and Lickliter J D, (2019). Phase I dose-escalation study to determine the safety, tolerability, preliminary efficacy and pharmacokinetics of an intratumoral injection of tigilanol tiglate (EBC-46). *EBioMedicine* 50:433-441.

Prise K M & O'Sullivan J M (2009). Radiation induced bystander signalling in cancer therapy. *Nature Reviews Cancer* 9: 351-30.

Schumacher T N & Schreiber R D (2015). Neoantigens in cancer therapy. *Science* 348: 69-73.

Yarchoan M, Hopkins A & Jaffee E M (2017). Tumor mutational burden and response rate to PD-1 inhibition. *New England Journal of Medicine* 377: 2500-2501.

The invention claimed is:

1. A method of stimulating tumour regression in at least one non-target tumour in a subject with multiple tumours, said method comprising administering to at least one target tumour a 6,7-epoxytiglienone compound or a pharmaceutically acceptable salt thereof as a monotherapy; wherein the at least one target tumour and the at least one non-target tumour are immunogenic tumours, and wherein administration is localised administration to the at least one target tumour; wherein the 6,7-epoxytiglienone compound is a compound of formula (I):

(I)

or a geometric isomer or stereoisomer or a pharmaceutically acceptable salt thereof;

wherein $R_1$ is hydrogen or $C_{1-6}$alkyl;

$R_2$ is —$OR_9$;

$R_3$ is —OH or —$OR_9$;

$R_4$ and $R_5$ are independently selected from hydrogen and $C_{1-6}$alkyl;

$R_6$ is hydrogen or —$R_{10}$;

$R_7$ is hydroxy or —$OR_{10}$;

$R_8$ is hydrogen or $C_{1-6}$alkyl;

$R_9$ is —$C_{1-20}$alkyl, —$C_{2-20}$alkenyl, —$C_{2-20}$alkynyl, —C(O)$C_{1-20}$alkyl, —C(O)$C_{2-20}$alkenyl, —C(O)$C_{2-20}$alkynyl, —C(O)cycloalkyl, —C(O)$C_{1-10}$alkylcycloalkyl; —C(O)$C_{2-10}$alkenylcycloalkyl, —C(O)$C_{2-10}$alkynylcycloalkyl, —C(O) aryl, —C(O)$C_{1-10}$alkylaryl, —C(O)$C_{2-10}$alkenylaryl, —C(O)$C_{2-10}$alkynylaryl, —C(O)$C_{1-10}$alkylC (O) $R_{11}$, —C(O)$C_{2-10}$alkenylC (O) $R_{11}$, —C(O)$C_{2-10}$alkynylC (O) $R_{11}$, —C(O)$C_{1-10}$alkylCH ($OR_{11}$) ($OR_{11}$), —C(O)$C_{2-10}$alkenylCH ($OR_{11}$) ($OR_{11}$), —C(O)$C_{2-10}$alkynylCH ($OR_{11}$) ($OR_{11}$), —C(O)$C_{1-10}$alkylS$R_{11}$, —C(O)$C_{2-10}$alkenylS$R_{11}$, —C(O)$C_{2-10}$alkynylS$R_{11}$, —C(O)$C_{1-10}$alkylC(O)$OR_{11}$, —C(O)$C_{2-10}$alkenylC(O)$OR_{11}$, —C(O)$C_{2-10}$alkynylC(O)$OR_{11}$, —C(O)$C_{1-10}$alkylC(O)S$R_{11}$, —C(O)$C_{2-10}$alkenylC(O)S$R_{11}$, —C(O)$C_{2-10}$alkynylC(O)S$R_{11}$, $R_{10}$ is —$C_{1-6}$alkyl, —$C_{2-6}$alkenyl, —$C_{2-6}$alkynyl, —C(O)$C_{1-6}$alkyl, —C(O)$C_{2-6}$alkenyl, —C(O)$C_{2-6}$alkynyl, —C(O) aryl, —C(O)$C_{1-6}$alkylaryl, —C(O)$C_{2-6}$alkenylaryl, —C(O)$C_{2-6}$alkynylaryl; and $R_{11}$ is hydrogen, —$C_{1-10}$alkyl, —$C_{2-10}$alkenyl, —$C_{2-10}$alkynyl, cycloalkyl or aryl;

wherein each alkyl, alkenyl, alkynyl, cycloalkyl or aryl group is optionally substituted.

2. The method of claim 1 wherein the 6,7-epoxytiglienone compound or a pharmaceutically acceptable salt thereof is administered to one target tumour.

3. The method of claim 1 wherein the 6,7-epoxytiglienone compound or a pharmaceutically acceptable salt thereof is administered to more than one target tumour.

4. The method of claim 1 wherein the at least one target tumour comprises a primary tumour, a secondary tumour or a primary tumour and one or more secondary tumours.

5. The method of claim 1 wherein the target tumour is a secondary tumour.

6. The method of claim 1 wherein the at least one non-target tumour is a single tumour.

7. The method of claim 1 wherein the at least one non-target tumour is more than one tumour.

8. The method of claim 1 wherein the at least one non-target tumour is at least one bystander tumour, at least one tumour susceptible to an abscopal effect or at least one bystander tumour and at least one tumour susceptible to an abscopal effect.

9. The method of claim 8 wherein the at least one non-target tumour is susceptible to an abscopal effect.

10. The method of claim 1 wherein the localized administration is topical administration or intratumoural administration.

11. The method of claim 10 wherein the localized administration is intratumoural administration.

12. The method of claim 1 wherein the immunogenic tumour is selected from a melanoma, a basal cell carcinoma, a squamous cell carcinoma, a Merkel cell carcinoma, a lung carcinoma, a bladder carcinoma, a lymphoma, a breast adenocarcinoma, a hepatocellular carcinoma, a renal cell carcinoma, a medullary carcinoma, a colorectal cancer, a histiocytic sarcoma, a haemangiosarcoma or a mastocytoma.

13. The method according to claim 1 wherein one or more of the following applies:

i) $R_1$ is —$C_{1-3}$alkyl;

ii) $R_2$ and $R_3$ are independently selected from —OC(O)$C_{1-20}$alkyl, —OC(O)$C_{2-20}$alkenyl, —OC(O)$C_{2-20}$alkynyl, —OC(O)cycloalkyl, —OC(O)$C_{1-10}$alkylcycloalkyl; —OC(O)$C_{2-10}$alkenylcycloalkyl, —OC(O)$C_{2-10}$alkynylcycloalkyl, —OC(O)aryl, —OC(O)$C_{1-10}$alkylaryl, —OC(O)$C_{2-10}$alkenylaryl, —OC(O)$C_{2-10}$alkynylaryl, —OC(O)$C_{1-10}$alkylC (O) $R_{11}$, —OC(O)$C_{2-10}$alkenylC (O) $R_{11}$, —OC(O)$C_{2-10}$alkynylC (O) $R_{11}$, —OC(O)$C_{1-10}$alkylCH ($OR_{11}$) ($OR_{11}$), —OC(O)$C_{2-10}$alkenylCH ($OR_{11}$) ($OR_{11}$), —OC(O)$C_{2-10}$alkynylCH ($OR_{11}$) ($OR_{11}$), —OC(O)$C_{1-10}$alkylS$R_{11}$, —OC(O)$C_{2-10}$alkenylS$R_{11}$, —OC(O)$C_{2-10}$alkynylS$R_{11}$, —OC(O)$C_{1-10}$alkylC(O)$OR_{11}$, —OC(O)$C_{2-10}$alkenylC(O)$OR_{11}$, —OC(O)$C_{2-10}$alkynylC(O)$OR_{11}$, —OC(O)$C_{1-10}$alkylC(O)S$R_{11}$, —OC(O)$C_{2-10}$alkenylC(O)S$R_{11}$ or —OC(O)$C_{2-10}$alkynylC(O)S$R_{11}$;

iii) $R_4$ and $R_5$ are independently selected from —$C_{1-3}$alkyl;

iv) $R_6$ is hydrogen, —C(O)$C_{1-6}$alkyl, —C(O)$C_{2-6}$alkenyl, —C(O)$C_{2-6}$alkynyl or —C(O) aryl;

v) $R_7$ is hydroxyl, —OC(O)$C_{1-6}$alkyl, —OC(O)$C_{2-6}$alkenyl or —OC(O)$C_{2-6}$alkynyl, and vi) $R_8$ is —$C_{1-3}$alkyl.

14. The method of claim 13 wherein one or more of the following applies:
  i) $R_1$ is —$CH_3$;
  ii) $R_2$ and $R_3$ are independently selected from —OC(O)$C_{1-6}$alkyl, —OC(O)$C_{2-6}$alkenyl or —OC(O)$C_{2-6}$alkynyl;
  iii) $R_4$ and $R_5$ are each —$CH_3$;
  iv) $R_6$ is hydrogen, —C(O)$C_{1-3}$alkyl, —C(O)$C_{2-3}$alkenyl or —C(O)$C_{2-3}$alkynyl;
  v) $R_7$ is hydroxyl, —OC(O)$C_{1-3}$alkyl, —OC(O)$C_{2-3}$alkenyl or —OC(O)$C_{2-3}$alkynyl; and
  vi) $R_8$ is —$CH_3$.

15. The method according to claim 1 wherein the 6,7-epoxytiglienone compound is selected from:
  12-tigloyl-13-(2-methylbutanoyl)-6,7-epoxy-4,5,9,12,13,20-hexahydroxy-1-tiglien-3-one (Compound 1);
  12,13-di-(2-methylbutanoyl)-6,7-epoxy-4,5,9,12,13,20-hexahydroxy-1-tiglien-3-one (Compound 2);
  12-hexanoyl-13-(2-methylbutanoyl)-6,7-epoxy-4,5,9,12,13,20-hexahydroxy-1-tiglien-3-one (Compound 3);
  12,13-dihexanoyl-6,7-epoxy-4,5,9,12,13,20-hexahydroxy-1-tiglien-3-one (Compound 4);
  12-myristoyl-13-(2-methylbutanoyl)-6,7-epoxy-4,5,9,12,13,20-hexahydroxy-1-tiglien-3-one (Compound 5);
  12-tigloyl-13-(2-methylbutanoyl)-6,7-epoxy-4,5,9,12,13-pentahydroxy-20-acetyloxy-1-tiglien-3-one (Compound 6);
  12-myristoyl-13-acetyloxy-6,7-epoxy-4,5,9,12,13,20-hexahydroxy-1-tiglien-3-one (Compound 7);
  12-propanoyl-13-(2-methylbutanoyl)-6,7-epoxy-4,5,9,12,13,20-hexahydroxy-1-tiglien-3-one (Compound 8);
  12,13-ditigloyl-6,7-epoxy-4,5,9,12,13,20-hexahydroxy-1-tiglien-3-one (Compound 9);
  12-(2-methylbutanoyl)-13-tigloyl-6,7-epoxy-4,5,9,12,13,20-hexahydroxy-1-tiglien-3-one (Compound 10);
  12-butanoyl-13-(2-methylbutanoyl)-6,7-epoxy-4,5,9,12,13,20-hexahydroxy-1-tiglien-3-one (Compound 11);
  12-(3,3-dimethylbut-2-enoyl)-13-(2-methylbutanoyl)-6,7-epoxy-4,5,9,12,13,20-hexahydroxy-1-tiglien-3-one (Compound 12);
  12-hex-2,4-dienoyl-13-(2-methylbutanoyl)-6,7-epoxy-4,5,9,12,13,20-hexahydroxy-1-tiglien-3-one (Compound 13);
  12-tigloyl-13-(2-methylpropanoyl)-6,7-epoxy-4,5,9,12,13,20-hexahydroxy-1-tiglien-3-one (Compound 14);
  12-but-2-enoyl-13-(2-methylbutanoyl)-6,7-epoxy-4,5,9,12,13,20-hexahydroxy-1-tiglien-3-one (Compound 15);
  12-tigloyl-13-butanoyl-6,7-epoxy-4,5,9,12,13,20-hexahydroxy-1-tiglien-3-one (Compound 16);
  12,13-dibutanoyl-6,7-epoxy-4,5,9,12,13,20-hexahydroxy-1-tiglien-3-one (Compound 17);
  12,13-dipentanoyl-6,7-epoxy-4,5,9,12,13,20-hexahydroxy-1-tiglien-3-one (Compound 18);
  12,13-di-(2E,4E)-hexa-2,4-dienoyl-6,7-epoxy-4,5,9,12,13,20-hexahydroxy-1-tiglien-3-one (Compound 19);
  12,13-di-(2-methylbutanoyl)-6,7-epoxy-4,5,9,12,13,20-hexahydroxy-1-tiglien-3-one (Compound 20);
  12-(2-methylprop-2-enoyl)-13-(2-methylbutanoyl)-6,7-epoxy-4,5,9,12,13,20-hexahydroxy-1-tigliaen-3-one (Compound 21);
  12-(3-butenoyl)-13-nonanoyl-6,7-epoxy-4,5,9,12,13,20-hexahydroxy-1-tigliaen-3-one (Compound 22);
  12,13-di-nonoyl-6,7-epoxy-4,5,9,12,13,20-hexahydroxy-1-tigliaen-3-one (Compound 23);
  12,13-di-heptanoyl-6,7-epoxy-4,5,9,12,13,20-hexahydroxy-1-tigliaen-3-one (Compound 24);
  12,13-di-(3-methylbutanoyl)-6,7-epoxy-4,5,9,12,13,20-hexahydroxy-1-tigliaen-3-one (Compound 25);
  or a pharmaceutically acceptable salt thereof.

16. The method of claim 15 wherein the compound is 12-tigloyl-13-(2-methylbutanoyl)-6,7-epoxy-4,5,9,12,13,20-hexahydroxy-1-tiglien-3-one (Compound 1).

17. The method of claim 13, wherein $R_2$ and $R_3$ are independently selected from —OC(O)$C_{1-10}$alkyl, —OC(O)$C_{2-10}$alkenyl, —OC(O)$C_{2-10}$alkynyl, —OC(O)cycloalkyl, —OC(O)$C_{1-10}$alkylcycloalkyl; —OC(O)$C_{2-10}$alkenylcycloalkyl, —OC(O)$C_{2-10}$alkynylcycloalkyl or —OC(O)aryl.

* * * * *